(12) United States Patent
Mohamad Hani et al.

(10) Patent No.: US 9,962,089 B2
(45) Date of Patent: May 8, 2018

(54) METHODOLOGY AND APPARATUS FOR OBJECTIVE ASSESSMENT AND RATING OF PSORIASIS LESION THICKNESS USING DIGITAL IMAGING

(75) Inventors: Ahmad Fadzil Mohamad Hani, Perak (MY); Hurriyatul Fitriyah, Perak (MY)

(73) Assignee: INSTITUTE OF TECHNOLOGY PETRONAS SDN BHD, Perak (MY)

( * ) Notice: Subject to any disclaimer, the term of this patent is extended or adjusted under 35 U.S.C. 154(b) by 417 days.

(21) Appl. No.: 13/638,228

(22) PCT Filed: Mar. 25, 2011

(86) PCT No.: PCT/MY2011/000025
§ 371 (c)(1),
(2), (4) Date: Sep. 28, 2012

(87) PCT Pub. No.: WO2011/122936
PCT Pub. Date: Oct. 6, 2011

(65) Prior Publication Data
US 2013/0018271 A1  Jan. 17, 2013

(30) Foreign Application Priority Data

Mar. 29, 2010  (MY) .......................... PI 2010001386

(51) Int. Cl.
*A61B 6/00* (2006.01)
*A61B 5/00* (2006.01)
(Continued)

(52) U.S. Cl.
CPC .......... *A61B 5/0062* (2013.01); *A61B 5/0064* (2013.01); *A61B 5/441* (2013.01);
(Continued)

(58) Field of Classification Search
USPC ....... 600/407, 410, 411, 425, 427, 437, 438, 600/306; 382/128, 130, 131, 173, 254,
(Continued)

(56) References Cited

U.S. PATENT DOCUMENTS 5,319,549 A * 6/1994 Katsuragawa ........ G06T 7/0012
382/108
6,341,182 B1 * 1/2002 Fitzgerald .......... G01N 15/1475
382/205
(Continued)

FOREIGN PATENT DOCUMENTS

JP    2003-220037    8/2003

OTHER PUBLICATIONS

Ahmad Fadzil Mohamad Hani et al. 'Thickness Characterization of 3D Skin Surface Images Using Reference Kine construction Approach' Lecture Notes in Computer Science, 2009, vol. 5857/ 2009, pp. 448-454.

*Primary Examiner* — Amelie R Gillman
(74) *Attorney, Agent, or Firm* — Hamre, Schumann, Mueller & Larson, P.C.

(57) ABSTRACT

The present invention relates generally to a method and apparatus for assessing data from digital images of psoriasis lesion for said psoriasis lesion thickness by utilizing a developed computer vision system to obtain Psoriasis Area and Severity Index (PASI) parameters in particular.

8 Claims, 4 Drawing Sheets

(51) Int. Cl.
 *G06T 7/00* (2017.01)
 *G06T 7/60* (2017.01)
 *G06T 7/11* (2017.01)

(52) U.S. Cl.
 CPC .............. *G06T 7/0012* (2013.01); *G06T 7/11* (2017.01); *G06T 7/60* (2013.01); *G06T 2207/10028* (2013.01); *G06T 2207/30088* (2013.01)

(58) Field of Classification Search
 USPC ........ 382/260–266, 270, 276–278, 285, 286, 382/293–294
 See application file for complete search history.

(56) References Cited

U.S. PATENT DOCUMENTS

| | | | |
|---|---|---|---|
| 7,359,748 B1* | 4/2008 | Drugge | 600/476 |
| 8,755,577 B2* | 6/2014 | Mohamad Hani et al. | 382/128 |
| 2007/0060784 A1 | 3/2007 | Ellis | |
| 2008/0143718 A1* | 6/2008 | Ray | G06K 9/4638 345/424 |
| 2011/0257492 A1* | 10/2011 | Greve et al. | 600/306 |

\* cited by examiner

| Score | PASI Thickness Description |
|---|---|
| 0 | None |
| 1 | Slight elevation |
| 2 | Moderate elevation with rounded or sloped edges |
| 3 | Marked elevation with marked sharp edges |
| 4 | Very marked elevation with very hard sharp edges |

METHODOLOGY AND APPARATUS FOR OBJECTIVE ASSESSMENT AND RATING OF PSORIASIS LESION THICKNESS USING DIGITAL IMAGING

1. TECHNICAL FIELD OF INVENTION

The present invention relates generally to a method and apparatus for assessing data from digital images of psoriasis lesion for said psoriasis lesion thickness by utilizing a developed computer vision system to obtain Psoriasis Area and Severity Index (PASI) parameters in particular.

2. BACKGROUND OF THE INVENTION

Psoriasis is common skin disease which is caused by speed-up replacement of human skin cell. In normal condition, skin cells shed and replace themselves in 21-28 days. But in psoriasis, this process can occur in 2-6 days. Psoriasis can affect any ages, any gender and regardless the race. Around 125 million of people around the worlds are affected, or 2-3% of population is living with psoriasis.

Psoriasis is non-contagious from person to person or between the patient's body part itself. Up to now, there is no solid inference that psoriasis can run in families. Several cases show that children whose parent is psoriasis patient also have psoriasis. But some cases reveal the opposite.

About 80% of psoriasis case is plaque psoriasis. This type sometimes is also named with psoriasis vulgaris as it means common. Plaque psoriasis appears with white scales in the top of red and thick patches. The white scales are the skin shedding as the effect of speed-up skin growth. The old scales can be shed by scratching. While the redness patches is due to the increase of blood vessels to support the increase of cell production.

Recent research has found that the change in skin growth is affected by the change in immune system. Certain immune cell (T cell) becomes triggered and overactive. T cell will act as if they were fighting virus, infection or healing the wound. This condition speed-up the skin growth at some body part hence thick plaque is formed. Psoriasis usually occurs in knee, elbow, and scalps, but it can also happen in any part of human body.

To cure psoriasis, physicians have 4 types of treatments. The drug used depends on the psoriasis severity level. For mild to moderate psoriasis, physicians give topical therapies. It is available in creams, lotions, ointments, mousses, and gels. The topical therapies are applied in localized psoriasis. The second treatment is phototherapy. This therapy uses ultraviolet light A (UVA) and B (UVB). Physicians will ask patient to have phototherapy session for several weeks. The third treatment is systemic medication which uses tablets or pills. This treatment have potential side effect to the patient body, hence only patient with moderate to severe psoriasis will undergo this treatment. The fourth or the latest treatment found is biological injection. This treatment only applied to patients with severe psoriasis which other types of treatment can not handle it. The injection will block certain immune cell (T cell) to act, as this speed-up growth is the cause of psoriasis.

Physicians use their knowledge and experience to decide which treatment to be applied. Patient's physical condition which differs from one another also gives extra thought to the physicians to decide it. This includes combination of several treatments, changing dosage and treatment change. In every visit, physicians assess the patient's psoriasis severity as well as monitor the treatment efficacy.

The gold standard to assess psoriasis condition is Psoriasis Area and Severity Index (PASI). In PASI, the human body is divided into four regions: head, trunk, upper extremities and lower extremities. There are 4 parameters that will be determined in every body regions which are psoriasis area, erythema (redness), thickness and scaliness. Each body regions is weighted differently regarding the proportion of body surface area (BSA). Head is weighted 0.1, trunk is 0.3, upper extremities is 0.2 and 0.4 for lower extremities. PASI scoring is calculated using equation below.

$$PASI=0.1(R_h+T_h+S_h)A_h+0.2(R_u+T_u+S_u)A_u+0.3(R_t+T_t+S_t)A_t+0.4(R_l+T_l+S_l)A_l$$

A=area (0-6), R=redness (0-4), T=thickness (0-4), S=scaliness (0-4).

h=head, u=upper extremities, t=trunk, l=lower extremities.

The total PASI score ranges from 0 to 72; higher score indicate more severe psoriasis condition. The treatment is considered effective if the PASI score is reduced by 75% from the initial score.

Although PASI is gold standard to assess the treatment efficacy, this method is rarely used in daily practice. Dermatologist has to assess all lesions and score them for each four parameters: area percentage, erythema, thickness and scaliness. Hence it is a tedious task to do.

To score the thickness of psoriasis lesion, dermatologist slides their index finger on it. They choose a representative lesion among every lesion in each body part; head, trunk, upper extremities and lower extremities. The tactile information from dermatologist's finger is then combined by their knowledge and experience to determine the score. Some dermatologists also access the average thickness PASI score by choosing the most common thickness from all the lesions in that area. This manual and subjective assessment may lead to inter-rater and intra-rater score variation, inaccuracy and inconsistency. Inter-rater variation is the different scores given by two dermatologists, while intra-rater variation is the different scores given by same dermatologist. To have such qualitative assessment, even one dermatologist is possible to give different score in one lesion if asked to conduct second assessment. Thus, objective and quantitative evaluation of psoriasis lesion thickness for PASI scoring is important in deciding the treatment efficacy.

Another method to assess and rate the severity of the psoriasis thickness is by performing biopsy, whereby the said psoriasis lesions are cut and analyzed physically. This is not recommended because it involves physical removal of the said psoriasis lesion even before knowing the severity of the said legion. If the severity is low enough that oral or ointment medication can cure said psoriasis lesion, then the initial step of cutting said lesion is really unnecessary.

The X-ray radiation has also been used to measure the psoriasis thickness. The radiation transmits through the patient's skin and creates a projection image. Due to the usage of X-ray, which has the possibility of exposing hazard radiation to patients, this method is not recommended for daily practice. Furthermore, the X-ray technology needs a skilled person to perform the acquisition.

Another technology used to assess psoriasis lesion thickness is ultrasound. The ultrasound frequency that is commonly used to perform the image acquisition is 15 MHz. Using ultrasound technology as an assessment tool also needs a skilled person to interpret the image and differentiate the skin layers.

It is therefore advantageous if the assessment of the psoriasis lesion thickness for PASI scoring could be objectively and accurately evaluated. This is important in deciding the treatment efficacy, especially in clinical trials. It is also advantageous if the assessment could be used in daily practice and performed by regular physicians.

The present invention overcomes the above shortcomings by providing a method and apparatus for assessing data from digital images of psoriasis lesion for said psoriasis lesion thickness by utilizing a developed computer vision system to obtain Psoriasis Area and Severity Index (PASI) parameters in particular.

3. SUMMARY OF THE INVENTION

Accordingly, it is the primary aim of the present invention to provide a method and apparatus for objective assessment of psoriasis lesion thickness based on digital image.

It is yet another objective of the present invention to provide a method and apparatus for objective assessment of psoriasis lesion thickness that is non-invasive.

It is yet another objective of the present invention to provide a method and apparatus for objective assessment of psoriasis lesion thickness wherein the assessment of thickness can be done objectively and consistently without being influenced by other characteristic of the lesion such as area, pattern and boundary.

It is yet another objective of the present invention to provide a method and apparatus for objective assessment of psoriasis lesion thickness that has the potential to minimize variations of PASI score due to inter-rater and intra-rater, thus making it more accurate.

It is yet another objective of the present invention to provide a method and apparatus for objective assessment of psoriasis lesion thickness that can be applied on any skin colour.

Other and further objects of the invention will become apparent with an understanding of the following detailed description of the invention or upon employment of the invention in practice.

According to a preferred embodiment of the present invention there is provided,

An apparatus for objective severity assessment of psoriasis lesion thickness comprising:
at least one 3D optical scanner, together with at least one scanner lead;
at least one electrical signal connecting means;
characterized in that
further comprises at least one any acceptable electronic processing means to capture and average out the subtraction result to determine the PASI thickness value.

In implementing the preferred embodiment there is provided,

A method for objective severity assessment of psoriasis lesion thickness using digital imaging comprising:
i. capturing 3D digital image of patient;
ii. averaging the subtraction result to determine PASI thickness value;
characterized in that
said averaging the subtraction result to determine PASI thickness value is done by the sub-steps of:
 a. converting said 3D image to 2D elevation map whereby the gray level intensity of the 2D elevation map corresponds to the elevation of the 3D image;
 b. segmenting normal skin from the psoriasis lesion;
 c. constructing lesion base in the estimated surface using polynomial surface fitting;
 d. subtracting the lesion from said lesion base;
 e. averaging said subtraction result to determine the PASI thickness value of psoriasis lesion.

4. BRIEF DESCRIPTION OF THE DRAWINGS

Other aspects of the present invention and their advantages will be discerned after studying the Detailed Description in conjunction with the accompanying drawings in which.

5. DETAILED DESCRIPTION OF THE DRAWINGS

In the following detailed description, numerous specific details are set forth in order to provide a thorough understanding of the invention. However, it will be understood by those or ordinary skill in the art that the invention may be practised without these specific details. In other instances, well known methods, procedures and/or components have not been described in detail so as not to obscure the invention.

The invention will be more clearly understood from the following description of the methods thereof, given by way of example only with reference to the accompanying drawings. In the descriptions that follow, like numerals represent like elements in all figures. For example, where the numeral (2) is used to refer to a particular element in one figure, the numeral (2) appearing in any other figure refers to the same element.

Figures 1, 2:
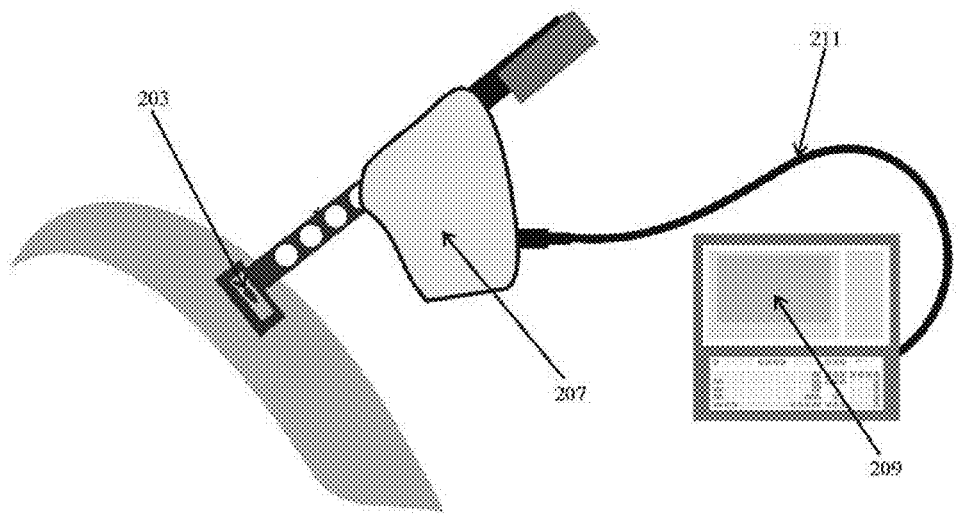
FIG. 1 is a table showing the description of each PASI lesion thickness score.
FIG. 2 shows a diagram of a 3D scanner connected to the computer with the software to obtain 3D image of psoriasis lesion.

Referring now to FIG. 1, there is a table showing the PASI thickness description. It is graded by score 0 to 4 with 0 for none elevation on skin and 4 for very marked elevation with very hard shape edges on skin. The other two parameters are graded by score 1 to 3 with higher score indicating more severe condition.

Referring now to FIG. 2, there is shown a scheme of a 3D scanner 207 connected to the computer 209 via scanner lead 211 with the software to obtain 3D image of psoriasis lesion 203. A non-contact 3D laser scanner is used to capture the images. The resolution that needs to be used should be high enough to perform the analysis using the said algorithm within an acceptable analysis timeframe. Nevertheless, other technology to capture 3D image such as optical can also be used to capture the said images. The setting must be set in order to meet the requirement of elevation accuracy of minimum 0.04 mm to perform the said algorithm. The optimal setting for the optical scanner should be approximately 64 um lateral resolution and 4 um depth resolution, but other settings can also be used as long as it meets the requirement of elevation accuracy of minimum 0.04 mm to perform the said algorithm. Images are taken with a fixed distance and a fixed picture size to avoid re-calibration of the system.

Figure 3:
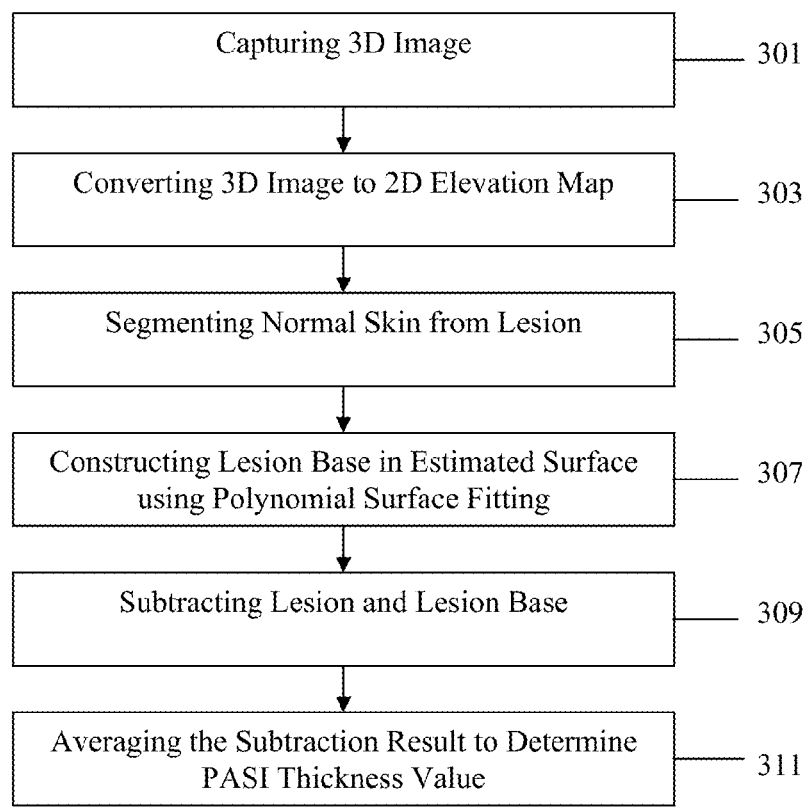
FIG. 3 is a flow chart showing a block diagram outlining the general step of psoriasis lesion thickness assessment.

Referring now to FIG. 3, there is shown flow chart outlining the general steps of psoriasis lesion thickness assessment to determine the score for PASI thickness comprising the first psoriasis lesion thickness assessment step indicated by the first block (301), the second psoriasis lesion thickness assessment step indicated by the second block (303), the third psoriasis lesion thickness assessment step indicated by the third block (305), the fourth psoriasis lesion thickness assessment step indicated by the fourth block (307), the fifth psoriasis lesion thickness assessment step indicated by the fifth block (309), and the last psoriasis lesion thickness assessment step indicated by the sixth block (311).

Figure 4A:
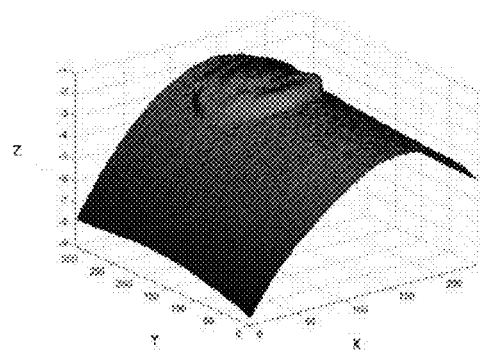
FIG. 4A to 4G shows the graphical images outlining the general steps of psoriasis lesion thickness assessment.

From the said flow chart, it can be seen that the first step is capturing 3D digital image as shown in FIG. 4A as indicated by the first block of FIG. 3 (301) using a 3D scanner device. The 3D image should consist of psoriasis lesion surrounded by a minimum 30% of normal skin. The patient's 3D image is taken using 3D scanner preferably an optical or laser scanner. During image capturing for laser scanner, the distance between patient skin and 3D scanner is kept minimum 1 meter to optimize the 3D image from shadow and blur. Other distance can also be used as long as it is within the allowed requirement of the said laser scanner. For optical scanner, it is a fixed distance according to the requirement of the said optical scanner.

Figure 4B:
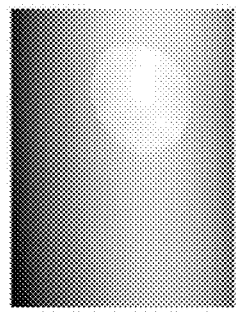

Each 3D image is converted to 2D elevation map which gives information of elevation in every X-Y coordinate. The elevations are shown as the gray-level intensity in the elevation map. The gray-level intensity corresponds to the elevation of the 3D image. The 2D elevation map of respective 3D image of FIG. 4A is shown in FIG. 4B. Converting 3D image to 2D elevation map is indicated by the second block of FIG. 3 (303).

Figure 4C:
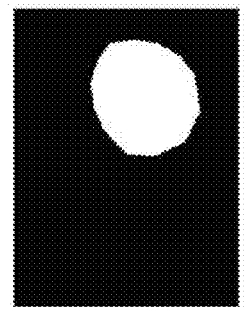
Figure 4D:
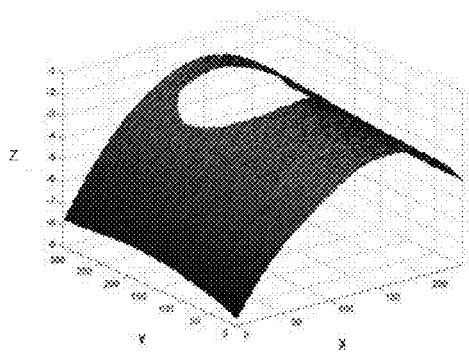
Figure 4E:
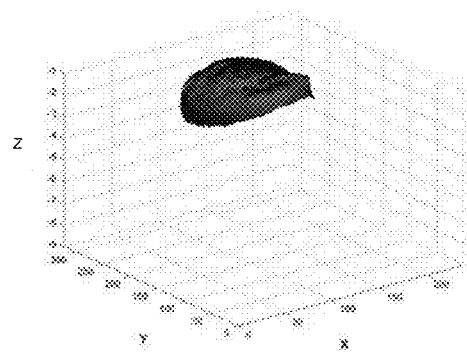

As the normal skin's gray-level intensity is lower compared to the lesion, which has higher gray-level intensity due to its elevation, the normal skin can be segmented accurately. The segmentation creates a masking in the 2D elevation map where normal skin is shown in black colour while lesion is shown in white colour. The segmentation of normal skin in 2D elevation map is shown in FIG. 4C. Using the segmentation, the normal skin coordinates are known. The normal skin coordinates are the used to obtain elevation value of respective coordinates in the 3D image. The segmented normal skin from the lesion in the 3D image is illustrated in FIG. 4D while the lesion itself is illustrated in FIG. 4E. This step is indicated by the third block of FIG. 3 (303).

Once the normal skin has been segmented from the lesion, the next step is constructing lesion base resulting in the estimated surface as indicated by the fourth block in FIG. 3 (307). The estimated surface is constructed using polynomial surface fitting.

Polynomial is chosen as surface fitting method since it is simple to apply. Polynomial is a best-fitting method that enables the constructed estimated surface to follow the curvature of surrounding normal skin. In the algorithm, the third order, fourth order and fifth order of polynomial are used. The equation for third order, fourth order and fifth order is shown in (1), (2) and (3), respectively.

$$Z = f(x,y) = (a_1 + a_2 x + a_3 x^2 + a_4 x^3) + (a_5 + a_6 x + a_7 x^2) y^1 + (a_8 + a_9 x) y^2 + (a_{10}) y^3 \quad (1)$$

$$Z = f(x,y) = (a_1 + a_2 x + a_3 x^2 + a_4 x^3 + a_5 x^4) + (a_6 + a_7 x + a_8 x^2 + a_9 x^3) y^1 + (a_{10} + a_{11} x + a_{12} x^2) y^2 + (a_{13} + a_{14} x) y^3 + (a_{15}) y^4 \quad (2)$$

$$Z = f(x,y) = (a_1 + a_2 x + a_3 x^2 + a_4 x^3 + a_5 x^4 + a_6 x^5)(a_7 + a_8 x + a_9 x^2 + a_{10} x^3 + a_{11} x^4) y + (a_{12} + a_{13} x + a_{14} x^2 + a_{15} x^3) y^2 + (a_{16} + a_{17} x + a_{18} x^2) y^3 + (a_{19} + a_{20} x) y^4 + (a_{21}) y^5 \quad (3)$$

Z as a function of f(x, y) is the elevation value, while a is the polynomial coefficient and x, y is the respective coordinate. Third order polynomial of surface fitting, fourth order polynomial and fifth order of polynomial has 10, 15 and 21 polynomial coefficients, respectively.

There are two steps to perform polynomial surface fitting. First is to find a matrix of polynomial coefficient using matrix equation as shown in (4) using every coordinate $[X_n, Y_n]$ and elevation value $[Z_n]$ of surrounding normal skin.

$$[a] = [X_n, Y_n]^{-1} [Z_n] \quad (4)$$

After obtaining the polynomial coefficients matrix [a], the elevation values of the estimated surface $[Z_e]$ in every coordinates $[X_e, Y_e]$ can be determined using (5).

$$[Z_i] = [X_i, Y_i][a] \quad (5)$$

Figure 4F:
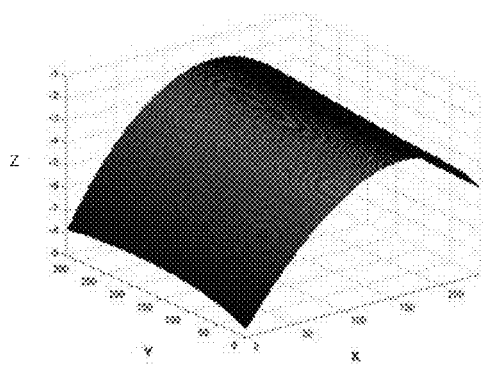
Figure 4G:
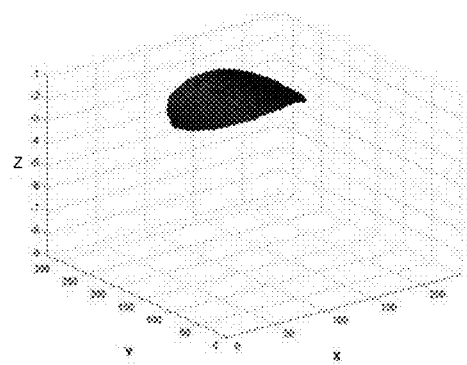

The constructed estimated surface using polynomial surface fitting is illustrated in FIG. 4F. The polynomial surface fitting is able to fit 4 types of curvature in human body. The curvature types are peak, pit, saddle ridge, saddle valley. The curvature is classified based on the sign of its Gaussian curvature (K) and mean curvature (H). Peak curvature has positive sign of K and negative sign of H. Pit curvature has positive sign of K and positive sign of H. Saddle ridge has negative sign of K and negative sign of H. Saddle valley has negative sign of K and positive sign of H. The lesion base is the elevation of the estimated surface on lesion's locations. The lesion base is illustrated in FIG. 4G.

Once the lesion base is constructed in the estimated surface, the lesion is then subtracted with the lesion base. Small number of negative value is possible to occur in the subtraction result. This happens since lesion is a very rough surface; hence there is possibility to have lower elevation of lesion compare to lesion base during the surface fitting. Those negative values are then excluded. This step is indicated by fifth block of FIG. 3 (309).

The subtraction result is then averaged to determine the PASI thickness value of the particular lesion. The mean is used as statistical parameter of averaging. This step is indicated by the sixth block of FIG. 3 (311).

While the preferred method of the present invention and its advantages has been disclosed in the above Detailed Description, the invention is not limited thereto but only by the spirit and scope of the appended claim.

What is claimed is:

1. A method for objectively assessing and rating a severity of a psoriasis lesion thickness using digital imaging, the method comprising:

capturing a 3D digital image of a patient using a 3D scanner, the 3D digital image including a psoriasis lesion and a minimum of 30% of normal skin surrounding the psoriasis lesion;

converting the 3D digital image to a 2D elevation map which provides elevation information corresponding to X-Y coordinates of the 3D digital image, the 2D elevation map showing a gray-level intensity that corresponds to the elevation information corresponding to the X-Y coordinates of the 3D digital image, the elevation information including elevation values at the X-Y coordinates of the 3D digital image;

segmenting the 3D digital image to define a segmented normal skin area in the 3D digital image, the segmented normal skin area including an area defined by the psoriasis lesion and the minimum of 30% of normal skin surrounding the psoriasis lesion;

electronically constructing a lesion base for the segmented normal skin area using a polynomial surface fitting including third, fourth, and fifth order polynomial surface fittings based on the X-Y coordinates of the 3D digital image and resulting in an estimated surface representing the lesion base, wherein the lesion base includes elevation values of the estimated surface at the X-Y coordinates of the 3D digital image, the elevation values of the estimated surface corresponding to a location of the psoriasis lesion in the 3D digital image;

subtracting the elevation values of the estimated surface at the X-Y coordinates of the 3D digital image from the elevation values at the X-Y coordinates of the 3D digital image to determine subtraction results at the X-Y coordinates of the 3D digital image; and averaging the subtraction results to determine a mean elevation value; and determining a Psoriasis Area and Severity Index (PAST) thickness value based on the mean elevation value.

2. The method according to claim 1, wherein the 3D scanner is one of a non-contact 3D laser scanner and an optical scanner.

3. The method according to claim 1, wherein the polynomial surface fitting includes:
finding a polynomial coefficient matrix from the X-Y coordinates of the 3D digital image.

4. The method according to claim 1, wherein the averaging further comprises:
excluding a negative value of the subtraction results.

5. The method according to claim 1, wherein the segmented normal skin area includes areas of normal skin that are contrastable against the lesion.

6. An apparatus for objectively assessing and rating a severity of a psoriasis lesion thickness, comprising:
at least one 3D scanner;
at least one scanner lead connected to the at least one 3D scanner; and
at least one electronic processor connected to the at least one 3D scanner,
wherein the electronic processor:
converts a 3D digital image to a 2D elevation map which provides elevation information corresponding to X-Y coordinates of the 3D digital image, the 2D elevation map showing a gray-level intensity that corresponds to the elevation information corresponding to the X-Y coordinates of the 3D digital image, the elevation information including elevation values at the X-Y coordinates of the 3D digital image, the 3D digital image including a psoriasis lesion and a minimum of 30% of normal skin surrounding the psoriasis lesion;

segments the 3D digital image to define a segmented normal skin area in the 3D digital image, the segmented normal skin area including an area defined by the psoriasis lesion and the minimum of 30% of normal skin surrounding the psoriasis lesion;

electronically constructs a lesion base for the segmented normal skin area using a polynomial surface fitting including third, fourth, and fifth order polynomial surface fittings based on the X-Y coordinates of the 3D digital image and resulting in an estimated surface representing the lesion base, wherein the lesion base includes elevation values of the estimated surface at the X-Y coordinates of the 3D digital image, the elevation values of the estimated surface corresponding to a location of the psoriasis lesion in the 3D digital image;

subtracts the elevation values of the estimated surface at the X-Y coordinates of the 3D digital image from the elevation values at the X-Y coordinates of the 3D digital image to determine subtraction results at the X-Y coordinates of the 3D digital image;

averages the subtraction results to determine a mean elevation value; and determines a Psoriasis Area and Severity Index (PAST) thickness value based on the mean elevation value.

7. The apparatus according to claim 6, wherein the 3D scanner is an optical scanner.

8. The apparatus according to claim 6, wherein the 3D scanner is a non-contact 3D laser scanner.

* * * * *